Figure 1:
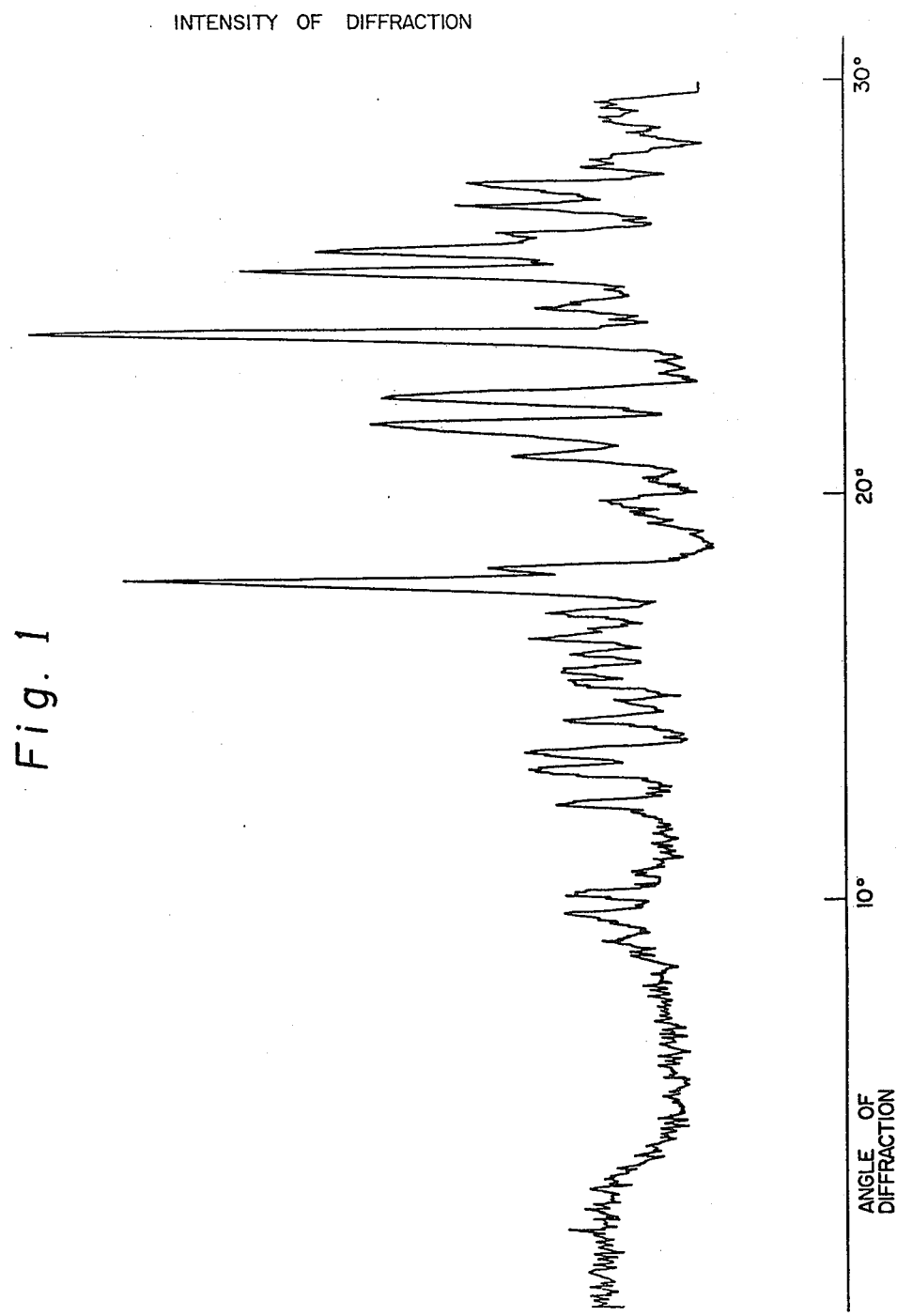

United States Patent [19]

Natsugari et al.

[11] 4,298,607
[45] Nov. 3, 1981

[54] CRYSTALLINE SALT OF 7β-[2-(2-AMINOTHIAZOL-4-YL)-(Z)-2-METHOXYIMINOACETAMIDO]-3-[(1-METHYL-1H-TETRAZOL-5-YL)THIOMETHYL]CEPH-3-EM-4-CARBOXYLIC ACID AND HCL OR HBR

[75] Inventors: Hideaki Natsugari, Hyogo; Iwao Mikami, Osaka; Michihiko Ochiai, Senriyamahigashi, all of Japan

[73] Assignee: Takeda Chemical Industries, Ltd., Osaka, Japan

[21] Appl. No.: 102,525

[22] Filed: Dec. 11, 1979

[30] Foreign Application Priority Data

Dec. 11, 1978 [JP] Japan .................................. 53-153377

[51] Int. Cl.$^3$ .................. A61K 31/545; C07D 501/56
[52] U.S. Cl. ...................................... 424/246; 544/27
[58] Field of Search ........................... 544/27; 424/246

[56] References Cited

U.S. PATENT DOCUMENTS 4,098,888  7/1978  Ochiai et al. ......................... 544/27
4,166,115  8/1979  Takaya et al. ........................ 544/27

OTHER PUBLICATIONS

Ochiai et al., Chem. Pharm. Bull., 25(11), 3115–3117 (1977), RS1C4.

Primary Examiner—Paul M. Coughlan, Jr.
Attorney, Agent, or Firm—Wenderoth, Lind & Ponack

[57] ABSTRACT

A crystalline hemi-acid salt comprising one molecule of 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid and a half molecule of HCl and HBr, is endowed with a high stability and suitable for an active component of an antimicrobial composition.

2 Claims, 2 Drawing Figures

CRYSTALLINE SALT OF 7β-[2-(2-AMINOTHIAZOL-4-YL)-(Z)-2-METHOXYIMINOACETAMIDO]-3-[(1-METHYL-1H-TETRAZOL-5-YL)THIOMETHYL]CEPH-3-EM-4-CARBOXYLIC ACID AND HCL OR HBR

This invention relates, in one aspect, to a crystalline hemi-acid salt comprising one molecule of 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid [hereinafter referred to as Compound (I)] and a half molecule of HCl or HBr and, in another aspect, to a method of producing the said hemi-acid salt.

The Compound (I) is a highly antibiotic compound [Ochiai, Aki, Morimoto, Okada and Matsushita: Chemical and Pharmaceutical Bulletin 25, 3115 (1977)]. This compound and other cephalosporin derivatives in general are unstable against heat, light, acid, alkali and so on, and it is generally accepted that utmost care must be paid in handling (isolating, purifying, storing, etc.) these compounds. The intensive studies done by the present inventors in this connection revealed that when Compound (I) is reacted with HCl or HBr, a crystalline hemi-acid salt comprising one molecule of Compound (I) and a half molecule of HCl or HBr is unexpectedly obtained, and that the crystalline hemi-acid salt thus formed is endowed with a high stability. This invention has been conceived and developed based on the above findings.

The crystalline hemi-acid salt comprising one molecule of Compound (I) and a half molecule of HCl or HBr is produced by reacting Compound (I), or a salt or an ester thereof, with HCl or HBr.

The Compound (I) may be used as it is, i.e. in the free form, or after converting by a routine means into the form of a salt, for example with an alkali metal (e.g. sodium, potassium, lithium, etc.), an alkaline earth metal (e.g. calcium, magnesium, etc.), an organic base (e.g. triethylamine, diethylamine, etc.) or an easily cleavable ester (e.g. silyl ester, etc.). The sodium salt is particularly expedient to use. The other starting material, HCl or HBr, may be used in gaseous form but, usually, is more conveniently used in a solution in a solvent such as water. Thus, hydrochloric acid and hydrobromic acid are usually employed. The reaction is generally conducted in a solvent. Most preferred solvent is water, but a mixture of water and one or more organic solvents may likewise be employed. The organic solvents may for example be $C_{1-5}$ alcohols such as methanol, ethanol, n-propanol, isopropanol, etc.; $C_{3-9}$ ketones such as acetone, methyl ethyl ketone, etc.; ethers such as tetrahydrofuran, dioxane, etc.; acetonitrile; and other water-soluble solvents. Ethanol and acetone are particularly preferable. The proportion of HCl or HBr depends on the form of the other starting material, the type of solvent, etc. but is at least a half mole to one mole of Compound (I), preferably up to 10 moles to one mole of Compound (I). Thus, when Compound (I) is employed in its free form, HCl or HBr is used in a proportion of 0.5 to 10 moles preferably 1 to 5 moles to one mole of Compound (I). When an alkali metal salt, an alkaline earth metal salt or an organic base salt of Compound (I) is employed, it is preferable to employ an additional 1 to 2 moles of HCl or HBr in order to convert such salt to the free form. The reaction is carried out usually at 0° to 40° C. and preferably at 10° to 30° C. The reaction time should vary with the purity of the starting materials and kind of impurities. When the purity of Compound (I), or a salt or an ester thereof, is for example 80 percent or higher, the reaction time is 30 minutes to 24 hours, and preferably 30 minutes to 16 hours. The reaction product can be isolated, for example by such procedures as filtration or centrifugation. Depending on the proportion of HCl or HBr and the kind or proportion of the solvent used, there are cases in which the obtained crystalline salt comprises one molecule of Compound (I) and one molecule of HCl or HBr. In such cases, the desired product can be easily obtained by contacting the crystalline salt with water, for example, by washing it with water or a mixture of water and one or more organic solvents. More particularly, the crystalline salt comprising one molecule of Compound (I) and one molecule of HCl or HBr, is washed with 5 to 50 times as much volume of water or a mixture of water and one or more organic solvents, or allowed to stand or stirred in a similar amount of water or a mixture of water and one or more organic solvents at 0° to 30° C. for 5 minutes to 2 hours to obtain the desired compound. It is thought that since the crystalline salt comprising one molecule of Compound (I) and one molecule of HCl or HBr is a salt of weak base, contacting the salt with an excess of water or a mixture of water and one or more organic solvents may result in a dissociation of the salt into Compound (I) and HCl or HBr, followed by a further transformation into the stable desired compound.

The resulting crystalline hemi-acid salt comprising one molecule of Compound (I) and a half molecule of HCl or HBr may contain water or/and organic solvent as a solvent of crystallization or as an adherent solvent, and such salt also falls within the scope of this invention. The amount of water thus contained is usually not more than 3 percent but the less the water thus contained, the higher is the stability of the crystals. The water content can be controlled by drying the crystals in the air or using a desiccant such as silica gel or phosphorus pentoxide under reduced pressure. The preferred water content is 0.05 to 1 percent and, for better results, 0.1 to 0.5 percent. When one or more organic solvents are contained, it may be removed if desired by bringing a humid gas or air into contact with the crystals in order to remove such solvents.

The contemplated compound thus obtained has been confirmed by elemental analysis to comprise one molecule of Compound (I) and a half molecule of HCl or HBr and by microscopic or polarizing-microscopic observation, X-ray diffraction and the like to be a crystalline substance. Moreover, the infrared absorption spectrum of the crystals shows sharp peaks which are not observed for amorphous powder. This crystalline hemi-acid salt comprising one molecule of Compound (I) and a half molecule of HCl or HBr is stable, does not change its crystalline form even by drying and besides sparingly dissolves in water, so that it offers many advantages such as a long storage life.

The crystalline hemi-acid salt according to this invention can be administered orally as it is or, alternatively, it can be used parenterally or externally in the form of a solution in distilled water with the aid of a nontoxic alkali hydroxide or alkali salt, e.g. sodium hydrogen carbonate, sodium carbonate, trisodium phosphate or the like adjusted the aqueous solution to a desired pH, ion type or ionic strength. For example, an aqueous solution containing ¾ mole of sodium carbonate to each mole of the crystalline hemi-acid salt can be used not only as an external disinfectant or sterilant in the disinfection of surgical equipment, sickrooms, drinking water, etc. but as a therapeutic agent in the following and other applications. Thus, for the purpose of treating infectious diseases caused by gram-positive bacteria (e.g. *Staphylococcus aureus*, etc.) or gram-negative bacteria (e.g. *Escherichia coli, Klebsiella pneumoniae, Proteus vulgaris, Proteus morganii*, etc.) in warm-blooded animals such as man, mouse, rat or dog, an aqueous solution prepared as above can be administered intramuscularly or intravenously. When such an aqueous solution as above is used as an external disinfectant for surgical instruments, it is prepared to contain 100γ as solvent-free product per milliliter and applied to the surgical instruments. For the treatment of urinary tract infections with *Escherichia coli* in man or mouse, the aqueous solution may be administered by the intravenous route in a daily dose of about 2.5 to 25 mg/kg as solvent-free product in 3 divided doses daily. Thus, the crystalline hemi-acid salt comprising Compound (I) and HCl or HBr and the nontoxic alkali hydroxide or alkali salt may be stored independently or in admixture, or under an inert gas or under reduced pressure in a sealed container. These products are extemporaneously dissolved in sterile distilled water or an equivalent.

The following Reference Examples and Examples are intended to illustrate this invention in further detail and should by no means be construed as limiting the scope of the invention. In this specification, the following abbreviations are used: microgram=mcg, milligram=mg, gram=g, milliliter=ml, liter=l, percent=%, minute=min., parts per million=ppm, Kilovolt=KV, milliampere=mA, Ångström=Å, Hertz=Hz, Megahertz=MHz, dimethylsulfoxide=DMSO, Figure=Fig., Infrared spectrum=IR, Nuclear Magnetic Resonance spectrum=NMR, Karl-Fischer Method=K.F.

Reference Example 1

Antimicrobial potency of the contemplated product as solvent-free form (Minimum Inhibitory Concentrations)

Antimicrobial spectrum (agar dilution)
*Staphylococcus aureus* FDA 209P:
 1.56 mcg/ml
*Staphylococcus aureus* 1840:
 3.13 mcg/ml
*Escherichia coli* NIHJ-2:
 0.1 mcg/ml
*Escherichia coli* O-111:
 0.024 mcg/ml
*Escherichia coli* T-7:
 0.39 mcg/ml
*Klebsiella pneumoniae* DT:
 0.024 mcg/ml
*Proteus vulgaris* IFO 3988:
 0.024 mcg/ml
*Proteus morganii* IFO 3168:
 0.1 mcg/ml
*Proteus mirabilis* GN4359:
 0.05 mcg/ml
*Proteus rettgeri* TN336:
 ≦0.012 mcg/ml
*Citrobacter freundii* GN1706:
 0.20 mcg/ml

REFERENCE EXAMPLE 2

250 Grams (potency) of the crystalline hemi-acid salt (composition: 1 mole of Compound (I) and ½ mole of HCl) and 42.7 g of sterile pure sodium carbonate are aseptically admixed and 500 mg (potency) aliquots of the mixture are filled into sterile vials of 12 ml capacity, which are then vacuum-sealed at 50 mmHg. The content of each vial is dissolved by addition of 2 ml of distilled water to prepare an injectable solution.

REFERENCE EXAMPLE 3

500 Grams (potency) of the crystalline hemi-acid salt (composition: 1 mole of Compound (I) and ½ mole of HCl) and 116.6 g of sterile pure sodium carbonate and 1,000 mg (potency) aliquots are dispensed into sterile vials of 28 ml capacity which are then vacuum-sealed at 50 mmHg. The content of each vial is dissolved by addition of 2 ml of distilled water to prepare an injectable solution.

It is considered that the crystalline hemi-acid salt comprising one molecule of Compound (I) and ½ molecule of HCl or HBr may assume tautomeric structures with respect to its 2-aminothiazol-4-yl group, i.e. the 2-aminothiazole form and the 2-iminothiazoline form. While this invention encompasses both of these tautomers, the 2-aminothiazole form is indicated in all references to this compound in this specification.

EXAMPLE 1

In 3.3 l of water is dissolved 165.0 g of sodium salt of 7β-[2-(2-minothiazol-4-yl)-(Z)-2-methoxyiminoacetamido]-3-[(1-methyl-1H-tetrazol-5-yl)thiomethyl]ceph-3-em-4-carboxylic acid and, while the solution is stirred at 25.5° C., 0.3 l of a 10% aqueous solution of HCl is added dropwise. In the course of dropwise addition, the abovementioned carboxylic acid separates out as a colorless precipitate and, then, dissolves. As this solution is stirred as it is for one hour, colorless crystals are formed. The crystals are collected by filtration (pH of filtrate 1.1), washed with water, drained well, dried over silica gel (blue) at 25° C. in a desiccator evacuated with a vacuum pump (about 1 mmHg) for 5 hours, and allowed to stand for 24 hours under the reduced pressure, whereby 154.5 g of the crystals of the said carboxylic acid-½ HCl are obtained.

Elemental analysis ($C_{16}H_{17}N_9O_5S_3.\frac{1}{2}HCl.\frac{1}{2}H_2O$):
Calcd.: C, 35.67; H, 3.46; N, 23.40; S, 17.85; Cl, 3.29;
Found: C, 35.78; H, 3.41; N, 23.46; S, 17.88; Cl, 3.46.

Water content (K.F.): 2.1% (calcd. 1.7%).

NMR (90 MHz, DMSO-$d_6$) δ: 3.54, 3.79(each 1H, doublet, J=18 Hz), 3.89(3H, singlet), 3.91(3H, singlet), 4.18, 4.36 (each 1H, doublet, J=13 Hz), 5.09 (each 1H, doublet, J=5 Hz), 5.71(1H, quartet, J=5, 9 Hz), 6.80(1H, singlet), 9.65(1H, doublet, J=9 Hz).

Figure 2:
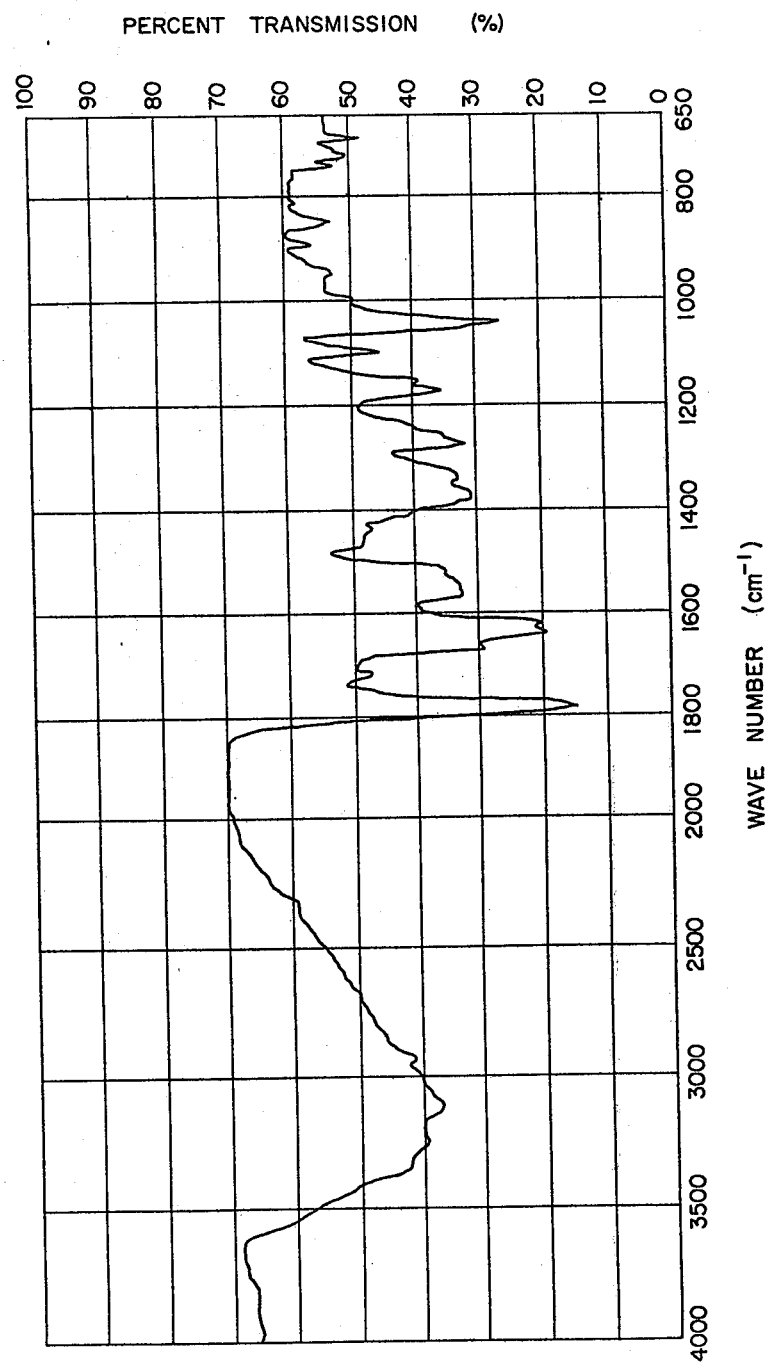

IR(KBr)cm$^{-1}$: 1780(β-lactam) (FIG. 2).

The powder X-ray diffraction pattern (FIG. 1; CuKα, 40 KV, 45 mA) of this product attests to its crystallinity, with interplanar spacings being 9.1 Å, 6.7 Å, 6.5 Å, 5.0 Å, 4.1 Å, 3.9 Å, 3.7 Å, 3.5 Å, 3.4 Å, 3.3 Å, 3.2 Å.

A portion of the above product is dried over $P_2O_5$ at 25° C. in a desiccator evacuated with a vacuum pump (about 1 mmHg) for 5 hours, and allowed to stand for 16 hours under the reduced pressure, whereby the water content is reduced to 0.3% (K.F.). The powder X-ray diffraction pattern and IR of this compound are in agreement with the pattern and spectrum of the abovementioned compound having a water content of 2.1%. The undecomposed portion of this compound after standing at 40° C. for a month was not less than 98%.

EXAMPLE 2

In 18 ml of water is suspended 1.00 g of 7β-[2-(2-aminothiazol-4-yl)-(Z)-2-methoxyiminoacetoamido]-3-[(1-methyl-1H-tetrazol-5-yl)thiomethyl]ceph-3-em-4-carboxylic acid, and under stirring at 25° C., 2 ml of a 10% aqueous solution of HCl is added. The resulting solution is stirred at that temperature for 30 minutes, whereupon colorless crystals separate out. The crystals are collected by filtration, washed with water and dried in the air. By the above procedure is obtained 0.73 g of the said carboxylic acid-½HCl salt [water content 3.2% (K.F.)].

In powder X-ray diffraction pattern and IR, this compound is in agreement with the compound according to Example 1.

EXAMPLE 3

In a mixture of 5 ml of acetone and 1 ml of water is dissolved 0.50 g of 7β-[2-(2-aminothiazol-4-yl)-(Z)-2-methoxyiminoacetamido]-3-[(1-methyl-1H-tetrazol-5-yl)-thiomethyl]ceph-3-em-4-carboxylic acid. While the solution is stirred at 23° C., 0.15 ml of a 10% aqueous solution of HCl is added. The mixture is stirred as it is for 1.5 hours and the resulting colorless crystals are collected by filtration, washed with acetone and dried over $P_2O_5$ at room temperature under reduced pressure (about 1 mmHg) for about 3 hours. By the above procedure is obtained 0.23 g of the said carboxylic acid-½HCl salt [water content 1.8% (K.F.)].

Elemental analysis ($C_{16}H_{17}N_9O_5S_3$.½HCl.½$H_2O$.1/6($CH_3)_2CO$: Calcd.: C, 36.13; H, 3.58; N, 22.98; S, 17.53; Cl, 3.23; Found: C, 36.51; H, 3.41; N, 23.35; S, 17.51; Cl, 2.81.

The NMR of this product shows that it is solvated with 1/6 mol of acetone. The powder X-ray diffraction pattern and IR of the above compound are in agreement with the pattern and spectrum of the compound obtained in Example 1.

EXAMPLE 4

In 10 ml of water is dissolved 0.50 g of sodium salt of 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid. While the solution is stirred at 23° C., 0.3 ml of a 48% aqueous solution of HBr is added. The resinous substance which has been obtained in a small amount is separated off and the remaining solution is stirred at 23° C. for 2 hours, whereby colorless crystals separate out. The crystals are collected by filtration, washed with water and dried over $P_2O_5$ at 23° C. under reduced pressure (about 1 mmHg) for about 10 hours. By the above procedure is obtained 0.27 g of the said carboxylic acid-½HBr [water content 0.3% (K.F.)]

Elemental analysis ($C_{16}H_{17}N_9O_5S_3$.½HBr): Calcd.: C, 34.81; H, 3.20; N, 22.84; Br, 7.24; Found: C, 34.71; H, 3.28; N, 22.82; Br, 6.90.

IR(KBr)cm$^{-1}$: 1780 (β-lactam).

The powder X-ray diffraction pattern of this product attests to its crystallinity.

EXAMPLE 5

In 20 ml of water is suspended 0.50 g of 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid and while the suspension is stirred at 23° C., 0.4 ml of a 48% aqueous solution of HBr is added. A small amount of insoluble material is filtered off and the filtrate is stirred at 23° C. for 16 hours. The resulting colorless crystals are collected by filtration, washed with water and dried over $P_2O_5$ at 23° C. under the reduced pressure (about 1 mmHg) for about 7 hours. By the above procedure is obtained 0.40 g of the said carboxylic acid-½HBr [water content 0.5% (K.F.)]

Elemental analysis ($C_{16}H_{17}N_9O_5S_3$.½HBr): Calcd.: C, 34.81; H, 3.20; N, 22.84; Br, 7.24; Found: C, 34.46; H, 3.31; N, 22.60; Br, 7.39.

In powder X-ray diffraction pattern and IR, this product is identical with the compound obtained in Example 4.

EXAMPLE 6

(1) In 720 ml of acetone is suspended 78.5 g of 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid, and under cooling at 5° C. and stirring, 72 ml of water is added. The solution thus obtained is filtered through Celite and washed with a mixture of acetone (65 ml) and water (3 ml). The filtrate and washings are combined and under cooling at 5° C. and stirring, 23 ml of 12 N HCl is added. The mixture is stirred for 1.5 hours and after removal of the cooling equipment, stirred further for 1.5 hours. The resulting colorless crystals are collected with a glass filter and washed with 500 ml of acetone. A humid nitrogen gas which is prepared by passing nitrogen gas through a bottle containing water, is passed over the above crystals at the rate of 1.9 l/min. to 3.3 l/min. for 10 hours. The crystals (water content 8.9% as measured for a sample by K.F.) were dried over silica gel (blue) in a desiccator under reduced pressure. By the above procedure is obtained 65.0 g of the said carboxylic acidmonohydrochloride.

Elemental analysis ($C_{16}H_{17}N_9O_5S_3$.HCl.1.5$H_2O$): Calcd.: C, 33.42; H, 3.68; N, 21.92; S, 16.73; Cl, 6.17; Found: C, 33.59; H, 3.56; N, 22.16; S, 16.79; Cl, 5.94.

This product contains 4.6% of water (K.F., calcd. 4.7%) and 110 ppm of acetone.

NMR (90 MHz, DMSO-$d_6$)δ: 3.57, 3.81(each 1H, doublet, J=18 Hz), 3.93(6H, singlet), 4.19, 4.38(each 1H, doublet, J=13 Hz), 5.12(1H, doublet, J=5 Hz), 5.73(1H, quartet, J=5, 9 Hz), 6.90(1H, singlet), 9.78(1H, doublet, J=5 Hz).

IR(KBr)cm$^{-1}$: 1770 (β-lactam).

The powder X-ray diffraction pattern of this product attests to its crystallinity.

(2) In 2 ml of water is suspended 0.20 g of the carboxylic acid-monohydrochloride obtained in (1) and the suspension is stirred at 26° C. for 10 minutes. (In the course of stirring, a change is observed in crystal form.) The resulting crystals are collected by filtration, washed with water and dried over $P_2O_5$ under the reduced pressure (about 1 mmHg) for about 5 hours. By the above procedure is obtained 0.17 g of the said carboxylic acid-½HCl [water content 0.9% (K.F.)]

Elemental analysis ($C_{16}H_{17}N_9O_5S_3$.½HCl.½$H_2O$): Calcd.: C, 35.97; H, 3.40; N, 23.59; Cl, 3.32; Found: C, 35.95; H, 3.11; N, 23.49; Cl, 3.08.

In power X-ray diffraction and IR, this product is identical with the compound obtained in Example 1.

What we claim is:

1. A crystalline hemi-acid salt which salt comprises 7β-[2-(2-aminothiazol-4-yl)-(Z)-2-methoxyiminoacetamido]-3-[(1-methyl-1H-tetrazol-5-yl)thiomethyl]ceph-3-em-4-carboxylic acid and HCl or HBr, of which the HCl or HBr content is a half mole per one mole of the former carboxylic acid.

2. An antibiotic composition in solid form which comprises a crystalline hemi-acid salt as defined in claim 1 and a nontoxic alkali salt selected from the group consisting of sodium carbonate, sodium hydrogen carbonate and trisodium phosphate.

* * * * *

UNITED STATES PATENT AND TRADEMARK OFFICE

CERTIFICATE EXTENDING PATENT TERM
UNDER 35 U.S.C. 156

Patent No.    : 4,298,607

Dated         : November 3, 1981

Inventor(s)   : Hideaki Natsugari et al

Patent Owner  : Takeda Chemical Industries, Ltd.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Twenty-Eighth day of December 1988.

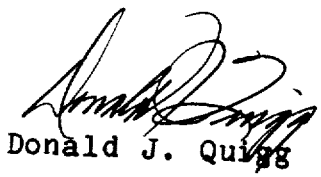

Donald J. Quigg

Assistant Secretary and Commissioner of Patents and Trademarks